United States Patent [19]

Davis et al.

[11] Patent Number: 4,610,988

[45] Date of Patent: Sep. 9, 1986

[54] 1-[3-(6-FLUORO-1,2-BENZISOXAZOL-3-YL)PROPYL]-4-(SUBSTITUTED)PIPERAZINES USEFUL FOR ALLEVIATING PAIN

[75] Inventors: Larry Davis, Sergeantsville; Joseph T. Klein, Somerville, both of N.J.

[73] Assignee: Hoechst-Roussel Pharmaceuticals Inc., Sommerville, N.J.

[21] Appl. No.: 742,350

[22] Filed: Jun. 7, 1985

Related U.S. Application Data

[62] Division of Ser. No. 366,248, Apr. 9, 1982, Pat. No. 4,536,578.

[51] Int. Cl.$^4$ .................. A61K 31/495; C07D 401/04; C07D 413/06
[52] U.S. Cl. .................. 514/253; 544/360; 544/364; 544/368
[58] Field of Search ................ 514/253; 544/360, 364, 544/368

[56] References Cited

U.S. PATENT DOCUMENTS

| | | | |
|---|---|---|---|
| 3,629,239 | 12/1971 | Kitahonoki et al. | 260/239 E |
| 3,732,306 | 5/1973 | Gutman et al. | 424/327 |
| 3,948,928 | 4/1976 | Nishimura et al. | 544/368 |
| 3,951,999 | 4/1976 | Gutman | 424/327 |
| 4,007,227 | 2/1977 | Baker | 564/254 |
| 4,122,176 | 10/1978 | Katsube et al. | 544/368 |
| 4,128,580 | 12/1978 | Matsumoto et al. | 564/254 |
| 4,172,896 | 10/1979 | Uno et al. | 424/272 |
| 4,235,914 | 11/1980 | Sasajima et al. | 544/392 |
| 4,396,770 | 8/1983 | Davis et al. | 546/198 |
| 4,536,578 | 8/1985 | Davis et al. | 544/360 |

FOREIGN PATENT DOCUMENTS

| | | |
|---|---|---|
| 40639 | 12/1981 | European Pat. Off. . |
| 684398 | 3/1965 | Italy . |
| 4970963 | 11/1972 | Japan . |
| 136666 | 11/1976 | Japan . |

OTHER PUBLICATIONS

Noller, Chem. of Organic Compounds, p. 169, 3rd edition, (1965).
Katritzky et al., Advances in Heterocyclic Chemistry, vol. 8, 284–285, 1967.
Uno et al., Chem. and Pharm. Bull. 24, 632, (1976).

*Primary Examiner*—Donald G. Daus
*Assistant Examiner*—Cecilia Shen
*Attorney, Agent, or Firm*—Raymond R. Wittekind

[57] ABSTRACT

Novel 1-[3-(6-fluoro-1,2-benzisoxazol-3-yl)propyl]-4-(substituted)piperazines, processes for the preparation thereof, and methods of treating psychoses, alleviating pain, and reducing blood pressure, employing compounds and compositions thereof are disclosed.

2 Claims, No Drawings

1-[3-(6-FLUORO-1,2-BENZISOXAZOL-3-YL)PROPYL]-4-(SUBSTITUTED)PIPERAZINES USEFUL FOR ALLEVIATING PAIN

This is a division of application Ser. No. 366,248 filed Apr. 9, 1982, now U.S. Pat. No. 4,536,578.

DESCRIPTION OF THE INVENTION

The present invention relates to novel 1-[(1,2-benzisoxazol-3-yl)propyl]piperazines. More particularly, the present invention relates to 1-[3-(6-fluoro-1,2-benzisoxazol-3-yl)propyl]-4-(substituted)piperazines of formula 1

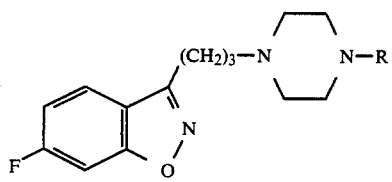

wherein R is loweralkyl, benzyl, 2-hydroxyethyl, pyridyl or a group of the formula

wherein $R_1$ is hydrogen, loweralkyl, loweralkoxy, halogen or trifluoromethyl; or pharmaceutically acceptable acid addition salts thereof, which are useful for treating psychoses, alleviating pain, and reducing blood pressure, alone or in combination with insert psychoses treating, pain alleviating, and blood pressure reducing adjuvants.

Preferred 1-[3-(6-fluoro-1,2-benzisoxazol-3-yl)propyl]-4-(substituted)piperazines of formula 1 are those wherein R is a group of the formula

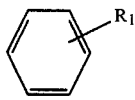

wherein $R_1$ is hydrogen, loweralkyl, loweralkoxy, halogen or trifluoromethyl. More preferred 1-[3-(6-fluoro-1,2-benzisoxazole-3-yl)propyl]-4-(substituted)piperazines are those wherein $R_1$ is loweralkoxy. Most preferred 1-[3-(6-fluoro-1,2-benzisoxazol-3-yl)propyl]-4-(substituted)piperazines are those wherein the loweralkoxy group is bound to the 2-position of the benzene ring.

As used through the specification and appended claims, the term "alkyl" refers to a straight or branched chain hydrocarbon radical containing no unsaturation and having 1 to 7 carbon atoms such as methyl, ethyl, 1-propyl, 2-propyl, 1-butyl, 1-pentyl, 2-pentyl, 3-hexyl, 4-heptyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy and the like; the term "halogen" refers to a member of the family consisting of chlorine, fluorine, bromine or iodine. The term "lower" as applied to any of the aforementioned groups refers to a group having a carbon skeleton containing up to and including 5 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of diastereomeric salts of those instant compounds characterized by the presence of a basic amino group and an optically active acid, or by the synthesis from optically active precursors.

The present invention comprehends all optical isomers and racemic forms thereof. The formulas of the compounds shown herein are intended to encompass all possible optical isomers of the compounds so depicted.

The novel 1-[3-(6-fluoro-1,2-benzisoxazol-3-yl)propyl]-4-(substituted)piperazines of formula 1, the compounds of the present invention, are prepared by condensing 3-(3-chloropropyl)-6-fluoro-1,2-benzisoxazole of formula 2

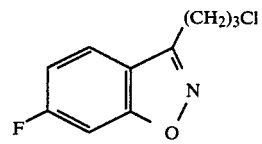

the synthesis of which is described in U.S. patent application Ser. No. 257,698, filed Apr. 27, 1981, with readily available piperazines of formula 3

wherein R is loweralkyl, benzyl, 2-hydroxyethyl, pyridyl or a group of the formula

wherein $R_1$ is hydrogen, loweralkyl, loweralkoxy, halogen or trifluoromethyl. The condensation is conveniently performed by treating the halide 2 with the piperazine 3 in the presence of an acid acceptor, a displacement promoter and a suitable solvent. Among acid acceptors, there may be mentioned alkali metal carbonates and alkali metal bicarbonates such as, for example, lithium carbonate, sodium carbonate and potassium carbonate, and lithium bicarbonate, sodium bicarbonate and potassium bicarbonate. Potassium carbonate and sodium bicarbonate are preferred. Among displacement promoters, there may be mentioned alkali metal halides such as, for example, sodium iodide and potassium iodide, and sodium bromide and potassium bromide. Potassium iodide is preferred. Among suitable solvents, there may be mentioned polar aprotic substances such as, for example, dimethylformamide, dimethylacetamide and hexamethylphosphoramide. Dimethylformamide is preferred. The temperature at which the condensation is conducted is not narrowly critical. It is desirable, however, to perform the condensation at a temperature within the range of about 50° C. to about 130° C. to assure a reasonable rate of conversion. A reaction temperature within the range of about 70° C. to 110° C. is preferred.

The 1-[(1,2-benzisoxazol-3-yl)propyl]piperazines of the present invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1957)]. Presented in Table I is the analgesic effect of some of the compounds of the invention, expressed as the subcutaneous dose at which 50% of the phenyl-para-quinone induced writhing is inhibited in the animals, i.e., the $ED_{50}$.

TABLE 1

| Compound | Analgesic Activity $ED_{50}$ (mg/kg) |
| --- | --- |
| 1-[3-(6-fluoro-1,2-benzisoxazol-3-yl)propyl]-4-(2-methoxyphenyl)-piperazine) dihydrochloride | 5.2 |
| 1-[3-(6-fluoro-1,2-benzisoxazol-3-yl)propyl]-4-(2-pyridyl)piperazine dihydrochloride | 0.8 |
| 1-[3-(6-fluoro-1,2-benzisoxazol-3-yl)propyl]-4-phenylpiperazine oxalate | 1.8 |
| propoxyphene | 3.9 |
| pentazocine | 1.3 |

Analgesia production is achieved when the present 1-[(1,2-benzisoxazol-3-yl)propyl]piperazines are administered to a subject requiring such treatment as an effective oral, parenteral or intravenous dose of from 0.1 to 50 mg/kg of body weight per day. A particularly effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-[(1,2-benzisoxazol-3-yl)propyl]piperazines of the present invention are also useful as antihypertensives due to their ability to reduce blood pressure in mammals. Antihypertensive activity is measured in the spontaneous hypertensive rat by the indirect tail cuff method described by A. Schwartz, Ed., "Methods in Pharmacology," Vol. 1, Appleton-Century-Crofts, New York, N.Y., 1971, page 135. According to this procedure, the test compound is administered intraperitoneally to a group of 4 rats for 3 days. The decrease in blood pressure is measured on the third day of administration. The antihypertensive activity, expressed as the decrease in mean arterial blood pressure (mm of mercury) in this procedure of some of the compounds of the present invention is presented in Table II.

TABLE II

| Compound | Dose (mg/kg of Body wt) | Blood Pressure Decrease (mm/mercury) |
| --- | --- | --- |
| 1-[3-(6-fluoro-1,2-benzisoxazol-3-yl)-propyl]-4-(2-pyridyl)-piperazine dihydrochloride | 50 | 66 |
| 1-[3-(6-fluoro-1,2-benzisoxazol-3-yl)-propyl]-4-phenylpiperazine oxalate | 50 | 38 |
| 1-[3-(6-fluoro-1,2-benzisoxazol-3-yl)-propyl]-4-(3-trifluoromethylphenyl)-piperazine hydrochloride | 50 | 66 |
| 4-(2-chlorophenyl)-1-[3-(6-fluoro-1,2-benzisoxazol-3-yl)-propyl]piperazine hydrochloride | 50 | 55 |
| 1-[3-(6-fluoro-1,2-benzisoxazol-3-yl)-propyl]-4-(2-methylphenyl)piperazine oxalate | 50 | 33 |
| 1-[3-(6-fluoro-1,2-benzisoxazol-3-yl)-propyl]-4-(4-fluorophenyl)piperazine oxalate | 50 | 33 |
| guanethidine | 50 | 20 |

Blood pressure reduction is achieved when the present 1-[(1,2-benzisoxazol-3-yl)propyl]piperazines are administered to a subject requiring such treatment as an effective oral, parenteral or intravenous dose of from 5.0 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-[(1,2-benzisoxazol-3-yl)propyl]piperazines of the present invention are useful for treating psychoses by virtue of their ability to block apomorphine-induced climbing in mammals.

Antipsychotic activity is determined in the climbing mice assay by a method similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice With: | Score |
| --- | --- |
| 4 paws on bottom (no climbing) | 0 |
| 2 paws on the wall (rearing) | 1 |
| 4 paws on the wall (full climb) | 2 |

Mice consistently climbing before the injection of apormorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally—apomorphine subcutaneously) is set to 100%. $ED_{50}$ values with 95% confidence limits are calculated by a Linear Regression Analysis. Antipsychotic activity expressed as the percentage decrease in climbing score of some of the instant 1-[(1,2-benzisoxazol-3-yl)propyl]-piperazines as well as standard antipsychotics are presented in Table III.

TABLE III

| Compound | Dose (mg/kg of body wt) | Antipsychotic Activity (% decrease in climbing score) |
|---|---|---|
| 1-[3-(6-fluoro-1,2-benz-isoxazol-3-yl)propyl]-4-(2-methoxyphenyl)piperazine dihydrochloride | 4.1 | 50 |
| 1-[3-(6-fluoro-1,2-benz-isoxazol-3-yl)propyl]-4-(2-pyridyl)piperazine dihydrochloride | 10 | 31 |
| 1-[3-(6-fluoro-1,2-benz-isoxazol-3-yl)propyl]-4-phenylpiperazine oxalate | 10 | 31 |
| haloperidol (standard) | 0.11 | 50 |
| thioridazine (standard) | 3.5 | 50 |

Antipsychotic activity of the 1-[(1,2-benzisoxazol-3-yl)propyl]piperazines of the present invention is also demonstrated by their ability to block conditioned avoidance in mammals in the Sidman Avoidance Paradigm by a method similar to that described by M. Sidman, Science, 118, 157 (1953).

The subjects are male squirrel monkeys (*Saimiri sciureus*). They are housed in individual home cages in the animal quarters for at least six weeks prior to training. When they are not in the test chambers, the subjects are maintained in their home cages with water available ad libitum and food available twice daily.

The apparatus consists of test cages (BRS/LVE) with a single lever and house-light. This is enclosed in a sound-attenuating chamber (BRS/LVE) with fan and the chambers are in an isolated room equipped with a speaker emitting a white-noise auditory background. The test cages have a grid floor of steel bars which are attached to a scrambled shock source (Coulbourn Instruments). The house-lights, shockers and response levers are controlled by BRS/LVE electromechanical timer and controls. The records of responses and shocks are recorded on Coulbourn print-out counters and Gerbrands cumulative recorders.

The monkeys are trained to avoid an unsignaled shock by repetitive lever-pressing responses. A shock (1.0 mA for 0.5 seconds) is delivered to the grid floor every 20 seconds if no responses are made (shock-shock interval of 20 seconds: SS-20″). A lever-press (response) will delay the oncoming shock for 20 seconds (Response-Shock interval of 20 seconds: RS-20′). The responses do not accumulate for delays of shock; a shock will be delivered for 20 seconds after the last response.

Every 15 minutes the total number of shocks received and the total number of responses made are accumulated and constitute the basic data. The animals are trained until they maintain a stable response-rate and are receiving no more than 50 shocks per 4 hour test session. After reaching these criteria of performance, experimental compounds are administered and their effects on the performance of this learned avoidance behavior are evaluated.

The drug's effect on performance of each animal is compared to the performance data generated in the previous non-drug session. Each animal thereby serves as its own control. The basic measures of performance during a specific time interval, responses and shocks, are used for evaluation. Responses are reported both as totals and as percent of control responses. Shocks are reported as totals and as shock-avoided (SHA) as percent of control. This latter measure is computed by subtracting the number of shocks received from the total number of possible shocks if no responses are made. For example, during a 15 minute period, a total of 45 shocks are possible and if a subject received 1 during the control session and 23 when treated with drug, $=(45-1)/45 \times 100 = 98\%$ SHA in control and $(45-23)/45 \times 100 = 49\%$ with drug and $49/98 \times 100 = 50\%$ SHA as percent of control. Since the monkeys are all good performers and receive few shocks in non-drug conditions if the drug effect on shock received were expressed as percent change in shocks, the reported results would be out of proportion to the actual effect. The above example would be expressed as a 2200% increase in shocks $[(23-1)/1 \times 100 = 2200\%]$.

The experimental compounds are administered by oral intubation immediately prior to testing in volumes of 1.0 cc/kg of body weight. The compounds are dissolved in distilled water or suspended with the addition of one drop of Tween-80 per 10 cc of solution.

In the initial screening of experimental compounds the results are reported in terms of the total effect during a 4-hour test. However, an $ED_{50}$ may be estimated during a representative time of peak activity.

Antipsychotic activity expressed as $ED_{50}$-values of a representative 1-[(1,2-benzisoxazol-3-yl)propyl]piperazine and two standards is presented in Table IV.

TABLE IV

| | Antipsychotic Activity | |
|---|---|---|
| Compound | Avoidance Response ($ED_{50}$ mg/kg of body wt) | Escape Response ($ED_{50}$ mg/kg of body wt) |
| 1-[3-(6-fluoro-1,2-benzisoxazol-3-yl)-propyl]-4-(2-methoxyphenyl)piperazine dihydrochloride | 2.9 | 4.8 |
| haloperidol (standard) | 1.21 | 1.27 |
| thioridazine (standard) | 2.6 | 3.5 |

The antipsychotic activity of the present 1-[(1,2-benzisoxazol-3-yl)propyl]piperazines is enhanced as a result of their unexpectedly reduced propensity to cause undesirable extrapyramidal side effects (extrapyramidal symptomatology) in mammals by a method similar to that described by J. Liebman and R. Neale, Psychopharmacology, 68, 25(1980).

Adult male squirrel monkeys (*Saimiri sciurens*) are housed in individual home cages and fed twice daily with water available "ad libitum" when they are not in the test chambers.

The test monkeys have been "primed" with once-weekly oral doses of haloperidol until they repeatedly demonstrated dyskinetic reactions upon drug administration. At this point, the monkeys were included in the test group and dosed orally with several standard drugs and experimental compounds to see if they elicited similar types of motor dysfunctions.

On the test day, drugs are administered by oral intubation immediately prior to testing in volumes of 1.0 cc/kg of body weight. The compounds are dissolved in distilled water or suspended with the addition of one drop of Tween-80 per 10 cc of solution.

After dosing, the monkeys are placed in observation chambers in an isolated room. Two experienced investigators observe the monkeys for dyskinetic symptomatology at 2, 4 and 6 hours postdose. They score the monkeys for the following specific dyskinetic symptomatology:

1. Circling—when the monkey rapidly circles the cage floor
2. "Duck walk"—when the monkey walks in a seated position with arms curled and held tightly to his side
3. Limb extension—an abnormal, prolonged extension of one or more limbs, similar to but of longer duration than a stretching motion
4. Pushing—the monkey will push against the cage wall with his head or body, frequently at the end of a circling episode
5. Writhing—slow, writhing movements of the whole body frequently in conjunction with a pushing episode
6. Oral dyskinesias—chewing, gnawing and abnormal tongue protrusions Normally, the monkey displays more than one type of dyskinesia during a test session but if any single dyskinesia is noted during an observation period, the monkey is given an overall positive E.P.S. score. The following scoring index is used in order to quantify the severity of symptoms:

---

SCORING INDEX FOR MONKEY EPS TEST
(DYSKINESIAS)

CIRCLING:
✓ 1 incidence of 5 or more revolutions (under 30 sec.)
✓✓ 2-4 incidences with one incidence over 30 seconds but under 1.5 minutes
✓✓✓ 5 or more incidences over 30 seconds each or one incidence over 1.5 minutes DUCK WALK:
✓ one incidence under 5 seconds
✓✓ 2-4 incidences each lasting between 5 seconds and 1.5 minutes
✓✓✓ 5 incidences or 1 incidence lasting over 1.5 minutes LIMB EXTENSIONS:
✓ 1-2 incidences under 10 seconds
✓✓ 3-5 incidences lasting between 10 seconds and 2 minutes
✓✓✓ 6 or more incidences or 1 incidence lasting over 2 minutes PUSHING/WRITHING:
✓ 1-2 incidences under 5 seconds each
✓✓ 3-5 incidences each lasting between 5 seconds and 30 seconds
✓✓✓ 6 incidences or 1 incidence lasting over 30 seconds

---

Extrapyramidal symptomatology of a representative 1-[(1,2-benzisoxazol-3-yl)propyl]piperazine of the present invention and two standards is given in Table V.

TABLE V

| Compound | Dose (mg/kg) body wt) | % Monkeys showing extrapyramidal symptoms |
|---|---|---|
| 1-[3-(6-fluoro-1,2-benzisoxazol-3-yl)propyl]-4-(2-methoxyphenyl)-piperazine dihydrochloride | 3.5* | 0 |
| | 5.0 | 0 |
| | 10.0 | 66 |
| haloperidol | 0.625 | 33 |
| | 1.3* | 100 |
| thioridazine | 3.5* | 100 |
| | 7.0 | 100 |

*ED$_{50}$-value in the Sidman Avoidance Paragidm in squirrel monkeys.

Antipsychotic activity is achieved when the present 1-[(1,2-benzisoxazol-3-yl)propyl]piperazines are administered to a subject requiring such treatment as an effective oral, parenteral or intravenous dose of from 0.1 to 50 mg/kg of body weight per day. A particularly preferred effective amount is about 5 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Effective amounts of the compounds of the invention may be administered to a subject by any one of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic cabocylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

1-[3-(6-Fluoro-1,2-benzisoxazol-3-yl)propyl]-4-(2-methoxyphenyl)piperazine dihydrochloride To 30 ml of dry dimethylformamide was added 2.9 g of 4-(2-methoxyphenylpiperazine), 3.4 g of 3-(3-chloropropyl)-6-fluoro-1,2-benzisoxazole, 8.0 g of sodium bicarbonate, and a few crystals of potassium iodide. The mixture was heated at 100° C. for two hrs, with stirring. The mixture was filtered and the filtrate was evaporated to an oil. The oil was stirred with 100 ml of water for five mins, and extracted with ether. The ether extract was washed with water (2×), saturated sodium chloride solution, and dried over anhydrous magnesium sulfate. After filtering, the solvent was evaporated to an oil. The oil was dissolved in ether, and treated with ethereal hydrogen chloride to give a salt. The salt was recrystallized from ethyl acetate/methanol/ether to yield 2.8 g (42%) of product, mp 208°–210° C. (dec).

ANALYSIS: Calculated for $C_{21}H_{24}FN_3O.2HCl$: 57.02%C; 5.93%H; 9.50%N; Found: 57.11%C; 6.05%H; 9.33%N.

EXAMPLE 2

1-[3-(6-Fluoro-1,2-benzisoxazol-3-yl)propyl]-4-phenylpiperazine oxalate

To 35 ml of dry dimethylformamide was added 1.6 g of 4-phenylpiperazine, 2.1 g of 3-(3-chloropropyl)-6-fluoro-1,2-benzisoxazole, 8.0 g of sodium bicarbonate, and a few crystals of potassium iodide. The mixture was heated at 100° C. for three hrs, with stirring. The mixture was filtered and the filtrate was evaporated to an oil. The oil was stirred with 100 ml of water for five mins and then extracted with ether. The ether extract was washed with water (2×), saturated sodium chloride solution, and dried over anhydrous magnesium sulfate. After filtering, the solution was converted to 4.0 g (70%) of product, by treatment with ethereal oxalic acid. Recrystallization twice from ethyl acetate/methanol/ether yielded the analytical sample mp 188°–190° C. (dec).

ANALYSIS: Calculated for $C_{20}H_{22}FN_3O.(CO_2H)_2$: 61.53%C; 5.63%H; 9.79%N; Found: 61.14%C; 5.52%H; 9.85%N.

EXAMPLE 3

1-[3-(6-Fluoro-1,2-benzisoxazol-3-yl)propyl]-4-(4-fluorophenyl)piperazine oxalate A mixture of 5.0 g of 3-(3-chloropropyl)-6-fluoro-1,2-benzisoxazole, 4.0 g of 1-(4-fluorophenyl)piperazine, 10 g of potassium carbonate and a few crystals potassium iodide in 70 ml of dimethylformamide was stirred at 80° C. for 4.5 hr. The mixture was cooled, filtered and concentrated to an oil, which was stirred with water and extracted with ethyl acetate-ether. The organic extracts were washed with water (2×), saturated sodium chloride solution, and dried over anhydrous magnesium sulfate. The mixture was filtered and concentrated. The residue was purified by column chromatography (silica gel, tetrahydrofuran) to give an oil. The oil was converted to 4.5 g (45%) of product by treatment with oxalic acid. Two recrystallizations from ethyl acetate/methanol gave the analytical sample, mo 186°–187° C. (dec).

ANALYSIS: Calculated for $C_{20}H_{21}F_2N_3O.(CO_2H)_2$: 59.05%C; 5.18%H; 9.39%N; Found: 58.83%C; 5.15%H; 9.37%N.

EXAMPLE 4

4-(2-Chlorophenyl)-1-[3-(6-fluoro-1,2-benzisoxazol-3-yl)propyl]piperazine hydrochloride To 40 ml of dimethylformamide was added, 5.0 g of 1-(2-chlorophenyl)piperazine hydrochloride hydrate, 6.4 g of 3-(3-chloropropyl)-6-fluoro-1,2-benzisoxazole, 10 g of milled potassium carbonate, and 0.01 g of potassium iodide, and the mixture was stirred at 90° C. for 2 hrs. The mixture was cooled, filtered and the filtrate evaporated to an oil. The oil was stirred with 100 ml water for five mins and then extracted with ether. The ether extract was washed with water (2×), saturated sodium chloride solution, and dried over anhydrous magnesium sulfate. After filtering, the solution was acidified to pH 1 with ethereal hydrogen chloride, and the precipitate was collected and dried to give 5.7 g (70%) of product, mp 195° C. (dec). Two recrystallizations from ethyl acetate/methanol (5:1) gave the analytical sample, mp 228° C. (dec).

ANALYSIS: Calculated for $C_{20}H_{21}ClFN_3O.HCl$: 58.54%C; 5.41%H; 10.24%N; 17.28%Cl; Found: 58.58%C; 5.37%H; 10.13%N; 17.04%Cl.

EXAMPLE 5

1-[3-(6-Fluoro-1,2-benzisoxazol-3-yl)propyl]-4-(3-trifluoromethylphenyl)piperazine hydrochloride A mixture of 6.5 g of 3-(3-chloropropyl)-6-fluoro-1,2-benzisoxazole, 5.8 g of N-(α,α,α-trifluoro-m-tolyl)piperazine, 7.0 g of potassium carbonate and a few crystals potassium iodide in 80 ml of dimethylformamide was stirred at 70°–75° C. for seven hrs. The reaction mixture was cooled, filtered and concentrated to an oil, which was stirred with water and extracted with ether-ethyl acetate. The organic extracts were washed with water (2×), saturated sodium chloride solution, and dried over anhydrous magnesium sulfate. The mixture was filtered and concentrated to an oil, which was converted to a salt by treatment with ethereal hydrogen chloride. The salt was recrystallized from ethyl acetate/methanol to give 4 g (35%) of product mp, 208°–209° C.

ANALYSIS: Calculated for $C_{21}H_{21}F_4N_3O.HCl$: 56.82%C; 5.00%H; 9.47%N; Found: 56.63%C; 4.98%H; 9.40%N.

EXAMPLE 6

1-[3-(6-Fluoro-1,2-benzisoxazol-3-yl)propyl]-4-(2-methylphenylpiperazine oxalate To 40 ml of dimethylformamide was added 5.0 g of 4-(2-methylphenyl)piperazine dihydrochloride, 6.4 g of 3-(3-chloropropyl)-6-fluoro-1,2-benzisoxazole, 10.0 g of milled potassium carbonate, and 0.01 g of potassium iodide. The mixture was stirred at 90° C. for two hrs, cooled, filtered, then evaporated to an oil. The oil was stirred with 100 ml water for ten min and extracted with ether. The ether extract was washed with water (2×), saturated sodium chloride solution and dried over anhydrous magnesium sulfate. After filtering, ethereal oxalic acid was added and the resulting precipitate was collected and dried to give 2.4 g (27%) of product. Two recrystallizations from ethyl acetate/methanol/ether gave the analytical sample, mp 177°–179° C.

ANALYSIS: Calculated for $C_{21}H_{24}FN_3O.(CO_2H)_2$: 62.29%C; 5.91%H; 9.48%N; Found: 62.03%C, 5.91%H; 9.36%N.

EXAMPLE 7

1-[3-(6-Fluoro-1,2-benzisoxazol-3-yl)propyl]-4-(3-methoxyphenyl)piperazine oxalate To 40 ml of dimethylformamide was added 5.3 g of 4-(3-methoxyphenyl)piperazine dihydrochloride, 6.4 g of 3-(3-chloropropyl)-6-fluoro-1,2-benzisoxazole, 10.0 g of milled potassium carbonate, and 0.01 g of potassium iodide. The mixture was stirred at 90° C. for two hrs, cooled, filtered, and evaporated to an oil. The oil was stirred with 100 ml water for ten mins, and extracted with ether. The ether extract was washed with water (2×), saturated sodium chloride solution and dried over anhydrous magnesium sulfate. After filtering, ethereal oxalic acid was added and the resulting precipitate was collected and dried to give 3.8 g (41%) of product. Two recrystallizations from ethyl acetate/methanol/ether (10:1:5), gave the analytical sample, mp 168° C. (dec).

ANALYSIS: Calculated for $C_{21}H_{24}FN_3O_2.(CO_2H)_2$: 60.12%C; 5.70%H; 9.15%N; Found: 60.01%C; 5.71%H; 9.06%N.

EXAMPLE 8

1-[3-(6-Fluoro-1,2-benzisoxazol-3-yl)propyl]-4-(4-methoxyphenyl)piperazine oxalate To 40 ml of dimethylformamide was added 4.3 g 3-(3-chloropropyl)-6-fluoro-1,2-benzisoxazole, 4.0 g of 4-(4-methoxyphenyl)piperazine dihydrochloride, 10.0 g of milled potassium carbonate, and 0.01 g potassium iodide. The mixture was stirred at 90° C. for two hrs, cooled, filtered, and the filtrate evaporated to an oil. The oil was stirred with 100 ml of water and extracted with ether. The ether extract was washed with water (2×), saturated sodium chloride solution and dried over anhydrous magnesium sulfate. After filtering, ethereal oxalic acid was added. The precipitate was collected and dried to yield 3.0 g (44%) of product. Two recrystallizations from ethyl acetate/methanol/ether (10:1:5) gave the analytical sample, mp 188°–189° C. (dec).

ANALYSIS: Calculated for $C_{21}H_{24}FN_3O_2.(CO_2H)_2$: 60.12%C; 5.70%H; 9.15%N; Found: 59.97%C; 5.76%H; 9.08%N.

EXAMPLE 9

1-[3-(6-Fluoro-1,2-benzisoxazol-3-yl)propyl]-4-(2-hydroxyethyl)piperazine dihydrochloride To 50 ml of dimethylformamide was added 2.6 g of 4-(2-hydroxyethyl)piperazine, 6.4 g of 3-(3-chloropropyl)-6-fluoro-1,2-benzisoxazole, 10.0 g of milled potassium carbonate, and 0.01 g of potassium iodide. The mixture was stirred at 90° C. for five hrs, cooled, filtered, and evaporated to an oil. The oil was stirred with 100 ml water for ten mins, and extracted with ether. The ether extract was washed with water (2×), saturated sodium chloride solution, and dried over anhydrous magnesium sulfate. After filtering, ethereal hydrogen chloride was added, and the precipitate was collected and dried to give 4.3 g (57%) of product. Two recrystallizations from ethyl acetate/methanol, gave the analytical sample, mp 228° C. (dec).

ANALYSIS: Calculated for $C_{16}H_{22}FN_3O_2.2HCl$: 50.53%C; 6.36%H; 11.05%N; Found: 50.35%C; 6.44%H; 10.86%N.

EXAMPLE 10

1-[3-(6-Fluoro-1,2-benzisoxazol-3-yl)propyl]-4-(2-pyridyl)piperazine dihydrochloride To 30 ml of dry dimethylformamide was added 2.45 g of 1-(2-pyridyl)piperazine, 3.4 g of 3-(3-chloropropyl)-6-fluoro-1,2-benzisoxazole, 8.0 g of sodium bicarbonate, and a few crystals of potassium iodide. The mixture was stirred at 100° C. for one and one-half hrs, filtered, the filtrate was evaporated to an oil. The oil was stirred with 100 ml water for five mins and extracted with ether. The ether extract was washed with water (2×), saturated sodium chloride and dried over anhydrous magnesium sulfate. After filtering, the solvent was evaporated to an oil, which was dissolved in ether, and converted to a salt by treatment with ethereal hydrogen chloride. The salt was recrystallized from ethyl acetate/methanol/ether to yield 3.0 g (48%) of product. Two recrystallizations from ethyl acetate/methanol/ether gave the analytical sample mp 235°–240° C. (dec).

ANALYSIS: Calculated for $C_{19}H_{21}FN_4O \cdot 2HCl$: 55.21%C; 5.60%H; 13.56%N; Found: 55.56%C; 5.55%H; 13.82%N.

EXAMPLE 11

1-[3-(6-Fluoro-1,2-benzisoxazol-3-yl)propyl]-4-methylpiperazine dihydrochloride To 30 ml of dry dimethylformamide was added 2.0 g of 4-methylpiperazine, 4.2 g of 3-(3-chloropropyl)-6-fluoro-1,2-benzisoxazole, 8.0 g of sodium bicarbonate and a few crystals of potassium iodide. After stirring at 100° C. for one and one-half hrs, the mixture was filtered. The filtrate was evaporated to an oil. The oil was stirred with 100 ml water for five mins and extracted with ether. The ether solution was washed with water (2×), saturated sodium chloride solution, dried over anhydrous magnesium sulfate and filtered. The filtrate was evaporated to an oil, which was dissolved in ether and converted to a salt by treatment with ethereal hydrogen chloride. Recrystallization from ethyl acetate/methanol/ether gave 3.2 g (46%) of product, mp 240° C. (dec). Recrystallization from ethyl acetate/methanol/ether gave the analytical sample, mp 245° (dec).

ANALYSIS: Calculated for $C_{15}H_{20}FN_3O \cdot 2HCl$: 51.43%C; 6.33%H; 12.00%N; Found: 51.26%C; 6.38%H; 11.82%N.

EXAMPLE 12

1-[3-(6-Fluoro-1,2-benzisoxazol-3-yl)propyl]-4-n-propylpiperazine dihydrochloride A mixture of 8.1 g of 3-(3-chloropropyl)-6-fluoro-1,2-benzisoxazole, 10 g of 1-n-propylpiperazine dihydrobromide, 15 g of potassium carbonate and a few crystals of potassium iodide in 80 ml of dimethylformamide was stirred at 70° C. for three hrs. The reaction mixture was cooled, filtered and concentrated to an oil, which was stirred with water and extracted with ether. The organic extracts were washed with water (2×), saturated sodium chloride solution, dried over anhydrous magnesium sulfate, and filtered. The filtrate was treated with ethereal hydrogen chloride to give 10 g (77%) of product, mp 250° C. (dec). The analytical sample was obtained by recrystallization from ethyl acetate/methanol and had mp 262° C. (dec).

ANALYSIS: Calculated for $C_{17}H_{24}FN_3O \cdot 2HCl$: 53.97%C; 6.93%H; 11.11%N; Found: 54.28%C; 6.90%H; 11.24%N.

EXAMPLE 13

1-[3-(6-Fluoro-1,2-benzisoxazol-3-yl)propyl]-4-n-butylpiperazine dihydrochloride A mixture of 12 g of 3-(-chloropropyl)-6-fluoro-1,2-benzisoxazole, 10 g of 1-n-butylpiperazine dihydrochloride, 21 g of potassium carbonate and a few crystals of potassium iodide in 80 ml of dimethylformamide was stirred at 70° C. for three hrs, cooled, filtered and concentrated to an oil. The oil was stirred with water and extracted with ether. The ether extracts were washed with water, saturated sodium chloride solution, dried over anhydrous magnesium sulfate, filtered and concentrated. The residue was converted to a salt by treatment with ethereal hydrogen chloride. Recrystallization from ethyl acetate/methanol gave 3.2 g (18%) of product, mp 260° C. (dec).

ANALYSIS: Calculated for $C_{18}H_{26}FN_3O \cdot 2HCl$: 55.10%C; 7.19%H; 10.71%N; Found: 55.20%C; 7.02%H; 10.79%N.

EXAMPLE 14

1-[3-(6-Fluoro-1,2-benzisoxazol-3-yl)propyl]-4-benzylpiperazine dihydrochloride A mixture of 13 g of 3-(3-chloropropyl)-6-fluoro-1,2-benzisoxazole, 10 g of 1-benzylpiperazine, 10 g of potassium carbonate and a few crystals potassium iodide in 80 ml of dimethylformamide, was stirred at ambient temperature for four hrs and then at 50° C. for one hr. The reaction mixture was cooled, filtered and concentrated to an oil, which was stirred with water and extracted with ether. The organic extracts were washed with water (2×), saturated sodium chloride solution, dried over anhydrous magnesium sulfate, filtered and concentrated. The residue was converted to 13 g (54%) of product, mp 235°–240° C., by treatment with ethereal hydrogen chloride. The analytical sample was obtained by recrystallization from acetate/methanol.

ANALYSIS: Calculated for $C_{21}H_{24}FN_3O \cdot 2HCl$: 59.16%C; 6.15%H; 9.86%N; Found: 58.90%C; 6.12%H; 9.80%N.

We claim:

1. A method of alleviating pain comprising administering to a mammal in need of pain alleviation a pain alleviating effective amount of a compound of the formula

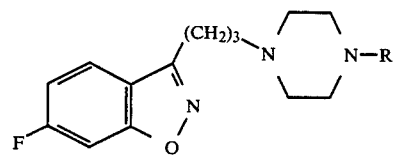

wherein R is loweralkyl, benzyl, 2-hydroxyethyl, pyridyl or a group of the formula

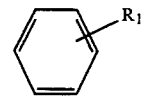

wherein $R_1$ is hydrogen, loweralkyl, loweralkoxy, halogen or trifluoromethyl; the optical antipodes thereof; or pharmaceutically acceptable acid addition salts thereof.

2. A pain alleviating or blood pressure reducing composition comprising an inert pain alleviating or blood pressure reducing adjuvant and, as the active ingredient, an amount effective in alleviating pain or reducing blood pressure of a compound of the formula

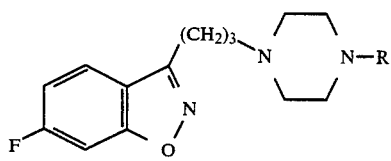

wherein R is loweralkyl, benzyl, 2-hydroxyethyl, pyridyl or a group of the formula

wherein $R_1$ is hydrogen, loweralkyl, loweralkoxy, halogen or trifluoromethyl; the optical antipodes thereof; or pharmaceutically acceptable acid addition salts thereof.

* * * * *